US008133699B2

(12) United States Patent
Chatellard et al.

(10) Patent No.: US 8,133,699 B2
(45) Date of Patent: Mar. 13, 2012

(54) MINIMAL DNA SEQUENCE ACTING AS A CHROMATIN INSULATOR AND ITS USE IN PROTEIN EXPRESSION

(75) Inventors: Philippe Chatellard, Lausanne (CH); Markus Imhof, Chexbres (CH)

(73) Assignee: Merk Serono S.A., Coinsins, Vaud (CH)

( * ) Notice: Subject to any disclaimer, the term of this patent is extended or adjusted under 35 U.S.C. 154(b) by 726 days.

(21) Appl. No.: 10/576,509

(22) PCT Filed: Oct. 20, 2004

(86) PCT No.: PCT/EP2004/052591
§ 371 (c)(1),
(2), (4) Date: Apr. 19, 2006

(87) PCT Pub. No.: WO2005/040384
PCT Pub. Date: May 6, 2005

(65) Prior Publication Data
US 2007/0134761 A1 Jun. 14, 2007

(30) Foreign Application Priority Data

Oct. 21, 2003 (EP) ..................... 03103890

(51) Int. Cl.
 C12P 21/06 (2006.01)
 C12P 21/04 (2006.01)
 C07H 21/04 (2006.01)
 C12N 5/00 (2006.01)
 C12N 5/02 (2006.01)
(52) U.S. Cl. ...... 435/69.1; 435/70.1; 435/325; 536/24.1
(58) Field of Classification Search ........................ None
See application file for complete search history.

(56) References Cited

U.S. PATENT DOCUMENTS

| | | | | |
|---|---|---|---|---|
| 6,113,898 A * | 9/2000 | Anderson et al. | .......... | 424/133.1 |
| 6,194,152 B1 * | 2/2001 | Laus et al. | .......... | 435/6 |
| 6,395,549 B1 * | 5/2002 | Tuan et al. | .......... | 435/455 |
| 6,432,700 B1 * | 8/2002 | Henderson et al. | .......... | 435/320.1 |
| 6,632,927 B2 * | 10/2003 | Adair et al. | .......... | 530/387.3 |
| 2007/0037734 A1 | 2/2007 | Rossi et al. | | |
| 2007/0196895 A1 | 8/2007 | Aloni et al. | | |
| 2007/0258962 A1 | 11/2007 | Chatellard et al. | | |
| 2007/0293658 A1 | 12/2007 | Kornmann et al. | | |
| 2008/0076708 A1 | 3/2008 | Altarocca et al. | | |

FOREIGN PATENT DOCUMENTS

| | | |
|---|---|---|
| WO | WO 01/02553 A3 | 1/2001 |
| WO | WO 2004/081167 A2 | 9/2004 |
| WO | WO 2004/101617 A1 | 11/2004 |
| WO | WO 2005/049649 A1 | 6/2005 |
| WO | WO 2005/083058 A1 | 9/2005 |
| WO | WO 2006/003134 A1 | 1/2006 |
| WO | WO 2006/128908 A1 | 12/2006 |
| WO | WO 2006/131550 A1 | 12/2006 |

OTHER PUBLICATIONS

Perlman, et al. (2003) The Journal of Clinical Endocrinology & Metabolism, 88(7): 3227-35.*
Aldrich, et al. (1998) Cytotechnology, 28: 9-17.*
Recillas-Targa, F. et al. "Position-effect protection and enhancer blocking by the chicken β-globin insulator are separable activities" *Proc. Natl. Acad. Sci. USA*, May 14, 2002, pp. 6883-6888, vol. 99, No. 10.
Bell, A. C. et al. "The protein CTCF is required for the enhancer blocking activity of vertebrae insulators" *Cell*, Aug. 6, 1999, pp. 387-396, vol. 98, No. 3.
Chung, J. H. et al. "Characterization of the chicken β-globin insulator" *Proc. Natl. Acad. Sci. USA*, Jan. 21, 1997, pp. 575-580, vol. 94, No. 2.
Pending claims in U.S. Appl. No. 11/916,087, filed Nov. 30, 2007, not yet published.
Pending claims in U.S. Appl. No. 11/915,453, filed Nov. 26, 2007, not yet published.
Burgess-Beusse, B. et al. "The Insulation of Genes From External Enhancers and Silencing Chromatin", *PNAS*, Dec. 10, 2002, pp. 16433-16437, vol. 99, Suppl. 4.
Chung, J. H. et al. "A 5' Element of the Chicken β-Globin Domain Serves as an Insulator in Human Erythroid Cells and Protects Against Position Effect in Drosophila", *Cell*, Aug. 13, 1993, pp. 505-514, vol. 74.
Ciana, P. et al. "Engineering of a Mouse for the in Vivo Profiling of Estrogen Receptor Activity", *Molecular Endocrinology*, 2001, pp. 1104-1113, vol. 15, No. 7.
Sun, F.-L. et al. "Putting Boundaries on Silence", *Cell*, Nov. 24, 1999, pp. 459-462, vol. 99.
Bell, A. C. et al. "Stopped at the Border: Boundaries and Insulators", *Current Opinion in Genetics & Development*, 1999, pp. 191-198, vol. 9.
Recillas-Targa, F. et al. "Positional Enhancer-Blocking Activity of the Chicken β-Globin Insulator in Transiently Transfected Cells", *PNAS*, Dec. 7, 1999, pp. 14354-14359, vol. 96, No. 25.
Izumi, M. et al. "Homogeneous Tetracycline-Regulatable Gene Expression in Mammalian Fibroblasts", *Journal of Cellular Biochemistry*, 1999, pp. 280-289, vol. 76.
De Wet, J. R. et al. "Cloning of Firefly Luciferase cDNA and the Expression of Active Luciferase in *Eschericia coli*", *Proc. Natl. Acad. Sci. USA*, Dec. 1985, pp. 7870-7873, vol. 82.
Wood, K. V. et al. "Synthesis of Active Firefly Luciferase by in Vitro Translation of RNA Obtained From Adult Lanterns", *Biochemical and Biophysical Research Communications*, Oct. 30, 1984, pp. 592-596, vol. 124, No. 2.
Blackwood, E. M. et al. "Going the Distance: A Current View of Enhancer Action", *Science*, Jul. 3, 1998, pp. 60-63, vol. 281.
Li, Q. et al. "Locus Control Regions Coming of Age at a Decade Plus", *TIG*, Oct. 1999, pp. 403-408, vol. 15, No. 10.
Mazumder, B. et al. "Translational Control by the 3'-UTR: The Ends Specify the Means", *Trends in Biochemical Sciences*, Feb. 2003, pp. 91-98, vol. 28, No. 2.

(Continued)

*Primary Examiner* — Robert M Kelly
(74) *Attorney, Agent, or Firm* — Saliwanchik, Lloyd & Eisenschenk (57) ABSTRACT

The invention relates to expression vectors comprising a DNA sequence of 146 bp capable of acting as chromatin insulator, to host cells containing such vectors, to a method of producing a desired polypeptide by using vectors containing said sequence and to the use of said DNA sequence.

19 Claims, 2 Drawing Sheets

OTHER PUBLICATIONS

Mountford, P. S. et al. "Internal Ribosome Entry Sites and Dicistronic RNAs in Mammalian Transgenesis", *TIG*, May 1995, pp. 179-184, vol. 11, No. 5.

Schümperli, D. et al. "Efficient Expression of *Escherichia coli* Galactokinase Gene in Mammalian Cells", *Proc. Natl. Acad. Sci. USA*, Jan. 1982, pp. 257-261, vol. 79.

Zhu, W.-Y. et al. "The Rate of Folate Receptor Alpha (FRα) Synthesis in Folate Depleted CHL Cells is Regulated by a Translational Mechanism Sensitive to Media Folate Levels, While Stable Overexpression of its mRNA is Mediated by Gene Amplification and an Increase in Transcript Half-Life", *Journal of Cellular Biochemistry*, 2001, pp. 205-219, vol. 81.

Assaraf, Y. G. et al. "Characterization of the Coexisting Multiple Mechanisms of Methotrexate Resistance in Mouse 3T6 R50 Fibroblasts", *The Journal of Biological Chemistry*, Mar. 25, 1992, pp. 5776-5784, vol. 267, No. 9.

Abbate, J. et al. "Bifunctional Protein Conferring Enhanced Green Fluorescence and Puromycin Resistance", *BioTechniques*, Aug. 2001, pp. 336-340, vol. 31, No. 2.

Shotwell, M. A. et al. "Regulation of Amino Acid Transport System L in Chinese Hamster Ovary Cells", *The Journal of Biological Chemistry*, Mar. 25, 1982, pp. 2974-2980, vol. 257, No. 6.

Kim, S.-H. et al. "Structural requirements of six naturally occurring isoforms of the IL-18 binding protein to inhibit IL-18" *PNAS*, Feb. 1, 2000, pp. 1190-1195, vol. 97, No. 3.

Novick, D. et al. "Interleukin-18 Binding Protein: A Novel Modulator of the Th1 Cytokine Response" *Immunity*, Jan. 1999, pp. 127-136, vol. 10.

Kim, S.-H. et al. "Structural requirements of six naturally occurring isoforms of the IL-18 binding protein to inhibit IL-18" *PNAS*, Feb. 1, 2000, pp. 1190-1195, vol. 97, No. 3.

Novick, D. et al. "Interleukin-18 Binding Protein: A Novel Modulator of the Th1 Cytokine Response" *Immunity*, Jan. 1999, pp. 127-136, vol. 10.

* cited by examiner

A ------------------------------------------------------------
B GAGCTCACGGGGACAGCCCCCCCCAAAGCCCCCAGGGATGTAATTACGTCCCTCCCCCG

A ------------------------------GCTCCGGTCCGGCGCTCCCCCCGCATCC
B CTAGGGGGCAGCAGCGAGCCGCCCGGGGCTCCGCTCCGGTCCGGCGCTCCCCCCGCATCC

A CCGAGCCGGCAGCGTGCGGGGACAGCCCGGGCACGGGGAAGGTGGCACGGGATCGCTTTC
B CCGAGCCGGCAGCGTGCGGGGACAGCCCGGGCACGGGGAAGGTGGCACGGGATCGCTTTC

A CTCTGAACGCTTCTCGCTG-TCTTTGAGCCTGCAGACACCTGGGGGATACGGGGAAAAA-
B CTCTGAACGCTTCTCGCTGCTCTTTGAGCCTGCAGACACCTGGGGGATACGGGGAAAAAG

A ----------
B CTTTAGGCTG

SEQUENCE LISTING

```
<160> NUMBER OF SEQ ID NOS: 2

<210> SEQ ID NO 1
<211> LENGTH: 146
<212> TYPE: DNA
<213> ORGANISM: Gallus gallus

<400> SEQUENCE: 1
gctccggtcc ggcgctcccc ccgcatcccc gagccggcag cgtgcgggga cagcccgggc    60
acggggaagg tggcacggga tcgctttcct ctgaacgctt ctcgctgtct ttgagcctgc   120
agacacctgg gggatacggg gaaaaa                                        146

<210> SEQ ID NO 2
<211> LENGTH: 250
<212> TYPE: DNA
<213> ORGANISM: Gallus gallus

<400> SEQUENCE: 2
gagctcacgg ggacagcccc cccccaaagc ccccagggat gtaattacgt ccctccccg     60 ctaggggca gcagcgagcc gcccggggct ccgctccggt ccggcgctcc ccccgcatcc   120
ccgagccggc agcgtgcggg gacagcccgg gcacggggaa ggtggcacgg gatcgctttc   180
ctctgaacgc ttctcgctgc tctttgagcc tgcagacacc tgggggatac ggggaaaaag   240
ctttaggctg                                                          250
```

MINIMAL DNA SEQUENCE ACTING AS A CHROMATIN INSULATOR AND ITS USE IN PROTEIN EXPRESSION

CROSS-REFERENCE TO RELATED APPLICATION

This application is the U.S. national stage application of International Patent Application No. PCT/EP2004/052591, filed Oct. 20, 2004, the disclosure of which is hereby incorporated by reference in its entirety, including all figures, tables and amino acid or nucleic acid sequences.

FIELD OF THE INVENTION

The invention relates to expression vectors comprising a DNA sequence of 146 bp capable of acting as chromatin insulator, to host cells containing such vectors, to a method of producing a desired polypeptide by using vectors containing said sequence and to the use of said DNA sequence.

BACKGROUND OF THE INVENTION

Introduction of genes into mammalian cells by transfection leads to their stable integration into the genome of host cells. Usually, this integration event is rare (<0.01%) and occurs in a random way regarding the locus of integration. Expression of the integrated transgene depends on the local environment. This means that nearby enhancers or silencers may affect the expression, and genes may become inactivated by spreading heterochromatin (chromatin position effect, CPE, also called silencing).

During the past years, studies begun in *Drosophila* and now extended to vertebrates, have identified DNA sequence elements called insulators that appear to function as "barrier", by preventing CPE, and/or as "enhancer blocking" having the capacity to shield a promoter from the action of a distal enhancer without preventing the enhancer from working on a proximal promoter. Thus, insulators are DNA sequence elements that protect transcribed regions from distant unrelated regulatory sequences.

The first DNA sequences described as having the properties of an insulator were scs (specialized chromosome structures) elements of *Drosophila*. Chung and Felsenfeld described an element, 5'HS4 (Dnase I-hypersensitive Site), acting as an insulator contained within a 1.2 kb DNA fragment derived from the 5' end of the chicken B-globin locus (Chung et al., 1993, U.S. Pat. No. 5,610,053). Much of the activity of the insulator was shown to be contained in a 250 bp fragment, the "core" region, that is included in the 5'HS4 sequence (Chung et al., 1997). The DNA of the core region was further dissected into five footprinted regions (FI-FV) and was shown to be GC-rich with the properties of a "CpG island", but did not appear to function as a promoter. Experiments showed that only one region, FII, was necessary for the enhancer blocking property and the purification of its binding proteins revealed that binding of CTCF (CCCTC-binding factor) was responsible for its activity (Bell et al., 1999).

In another study, the utility of the full 1.2 kb beta globin insulator element in protecting reporters form CPE has been demonstrated in in vivo assays including transgenic mice (Ciana et al., 2001). In CHO cell lines, Izumi and Gilbert showed that the presence of chromatin insulator sequences moderately improved stability but was not sufficient to produce homogeneous transformants (Izumi and Gilbert, 1999).

In a recent publication (Recillas-Targa et al., 2002) the functional activity of a 1.2 kb insulator element from the chicken beta-globin gene was reviewed. Besides working as efficient barrier to the activity of nearby enhancers or silencers, the 250 bp core element was shown to be sufficient to confer protection against silencing of genes caused by CPE and to provide long-term stable expression. Two copies of smaller fragments of the 250 bp core sequence essentially devoid of footprint region II, on each side of the reporter gene, were sufficient to confer protection from CPE, but not enhancer blocking, in chicken pre-erythroid 6C2 cells.

Since vector sizes should preferably not exceed 10 kb, there is a need to reduce the size of the regulatory elements present on these vectors. For instance, vector stability increases as the size of its DNA is reduced. Smaller vectors can accommodate larger segments of inserts. Moreover small elements simplify the modification of expression vectors and allow constructions where the total length of the insert must be limited.

It is therefore an object of this invention to provide a short DNA element that has insulator activity when used in vectors.

SUMMARY OF THE INVENTION

The present invention is based on the finding that a short DNA element of 146 bp, having the sequence of SEQ ID No: 1 is capable of acting as chromatin insulator. In the following, the insulator is called "the insulator of the invention" or just "the insulator". The number of transfected clones expressing the gene of interest was elevated when the constructs used included the insulator of the invention. The production of the polypeptide of interest was shown to be higher in expressing clones containing the insulator of the invention and long-term expression was shown to be stable.

Therefore, a first aspect of the invention relates to a DNA element having the sequence of SEQ ID No: 1.

A second aspect of the invention relates to a vector comprising one or more insulators of the invention.

A third aspect of the invention relates to a host cell comprising the insulator of the invention.

A fourth aspect of the invention relates to a host cell comprising a vector according to the invention.

In a fifth aspect of the invention, the host cell and the insulator of the invention are derived from different species.

A sixth aspect of the invention relates to a process for the production of a polypeptide of interest comprising the step of transfecting a host cell with a vector in accordance with the invention.

A seventh aspect of the invention relates to the use of a vector of the invention for the manufacture of a medicament for use in plasmid or DNA based therapy or gene therapy.

BRIEF DESCRIPTION OF THE DRAWINGS

The oval shape represents the polyadenylation signal. Insulator of the invention (filled circle), designated INS, tandem repeat flank each end of the expression cassette. B: same construct devoid of the insulators of the invention sequences.

DETAILED DESCRIPTION OF THE INVENTION

The present invention is based on the findings that a short DNA element of 146 bp, having the sequence of SEQ ID No: 1, is capable of acting efficiently as chromatin insulator when duplicated and inserted up and downstream of an expression unit. The presence of the insulator of the invention in transfection vectors significantly increased the number of clones expressing a marker gene. Furthermore, the pools comprising the insulated expression cassette had a significantly elevated productivity as compared to the control pool. In addition to that, the chance to obtain stable long-term expressing clones was also increased in the presence of the insulator of the invention.

Therefore, a first aspect of the invention relates to a DNA element, having the sequence of SEQ ID No: 1.

A second aspect of the invention related to a vector comprising one or more insulators of the invention.

The term "vector" refers to any carrier of exogenous DNA or RNA that is useful for transferring exogenous DNA to a host cell for replication and/or appropriate expression of the exogenous DNA by the host cell, such as e.g. plasmids, expression vectors, viral vectors etc.

Preferably, the vector further comprises a DNA element selected from:
a. an enhancer, or a functional expression enhancing fragment thereof,
b. a promoter domain or a functional expression promoting fragment thereof;
c. a DNA sequence coding for one or more polypeptides of interest.

An "Enhancer region" refers to a region of DNA which function is to augment or increase the transcription of one or more genes. Enhancers can usually function in either orientation and at various distances from the gene, or even within the gene. The person skilled in the art will further appreciate that the terms "promoter" (see below) and "enhancer" are not exactly defined and that thus the promoter may comprise enhancer regions, or enhancer regions may comprise promoter regions, depending on nomenclature and context.

The term "promoter" as used herein refers to a region of DNA that functions to control the transcription of one or more DNA sequences, and that is structurally identified by the presence of a binding site for DNA-dependent RNA-polymerase and of other DNA sequences, which interact to regulate promoter function. As mentioned above, an enhancer region may comprise all or part of a promoter as well.

A "functional expression promoting fragment", as used herein, of a promoter or an enhancer is a shortened or truncated promoter or enhancer sequence retaining the activity as a promoter or enhancer. Promoter or enhancer activity may be measured in any of the assays known in the art, e.g. in a reporter assay using Luciferase as reporter gene (de Wet et al., 1985; Wood et al., 1984), or commercially available from Promega®.

In a preferred embodiment, the vector comprises further elements regulating or influencing transcription or translation. Such elements may affect the process of transcription itself, processing, stability or translation efficiency of RNA. Examples for suitable elements are e.g. selected from the group consisting of 5'UTRs, introns, 3'UTRs (Mazumder et al., 2003), mRNA 3' end processing sequences e.g. polyadenylation sites, and IRES sequences for polycistronic expression (Mountford and Smith, 2003).

It is preferred to use an IRES element for expression of polycistronic mRNAs, in which the coding sequences are separated by the IRES. The advantage is that several polypeptides of interest may be expressed from the same mRNA and thus from the same promoter.

In a further preferred embodiment, the vector further comprises expression promoting sequences such as boundary elements, LCRs (e.g. described by Blackwood and Kadonaga, 1998) or matrix/scaffold attachment regions (e.g. described by Li et al., 1999) and elements for recombination and cassette exchange.

In yet a further preferred embodiment, the promoter comprised in the vector of the present invention may be of any cellular or of viral/phage origin such as SV40, hCMV, mCMV-IE1, mCMV-IE2, RSV, T7, T3, or a functional expression promoting fragment thereof.

Many polypeptides of interest may be expressed using a vector of the invention. The polypeptide of interest may be any polypeptide for which production is desired. For example, the polypeptide of interest may be, e.g., a naturally secreted protein, a normally cytoplasmic protein, a normally transmembrane protein, or a human or a humanized antibody. When the protein of interest is a normally cytoplasmic or a normally transmembrane protein, the protein has preferably been engineered in order to become soluble. The polypeptide of interest may be of any origin. Preferred polypeptides of interest are of human origin.

In preferred embodiments, the polypeptide is selected from the group consisting of chorionic gonadotropin (CG), follicle-stimulating hormone (FSH), lutropin-choriogonadotropic hormone (LH), thyroid stimulating hormone (TSH), growth hormone (GH), interferon receptors (e.g., IFNAR1, interferon gamma receptor), TNF receptors p55 (TNF binding protein I, TBP I) and p75 (TNF binding protein II, TBP II), interleukins (e.g., IL-6), interleukin binding proteins (e.g., IL-18BP), Leukemia Inhibitoiry factor (LIF), anti-CD11a antibodies, or muteins, fragments, soluble forms, functional derivatives, fusion proteins thereof.

"Interferon" or interferons are a subclass of cytokines that exhibit anti-inflammatory, antiviral and anti-proliferative activity. On the basis of biochemical and immunological properties, the naturally occurring human interferons are grouped into three classes: interferon alpha (leukocyte), interferon beta (fibroblast) and interferon gamma (immune). Alpha-interferon is currently approved in the United States and other countries for the treatment of hairy cell leukemia, venereal warts, Kaposi's Sarcoma (a cancer commonly afflicting patients suffering from Acquired Immune Deficiency Syndrome (AIDS)), and chronic non-A, non-B hepatitis.

Interferon gamma is a dimeric protein with subunits of 146 amino acids. It has antiviral and antiparasitic activities and also inhibits the proliferation of a number of normal and transformed cells.

In particular, human fibroblast interferon (IFN-β) has antiviral activity and can also stimulate natural killer cells against neoplastic cells. It is a polypeptide of 166 amino acids long and about 20 kDa. Rebif® (recombinant human Interferon-β) is the latest development in interferon therapy for multiple sclerosis (MS) and represents a significant advance in treatment. Rebif® is interferon (IFN)-beta 1a, produced from mammalian cell lines and virtually identical to the naturally occurring human molecule.

In a further preferred embodiment, other polypeptides of interest include, e.g., erythropoietin (EPO), granulocyte colony stimulating factor (G-CSF), granulocyte-macrophage colony-stimulating factor (GM-CSF), pituitary peptide hormones, menopausal gonadotropin, insulin-like growth factors (e.g., somatomedin-C), keratinocyte growth factor, glial cell line-derived neurotrophic factor, thrombomodulin, basic fibroblast growth factor, insulin, a coagulation factor (e.g. Factor VIII), somatropin, bone morphogenetic protein-2, platelet-derived growth factor, hirudin, epoietin, an integrin (e.g. LFA), recombinant LFA-3/IgG1 fusion protein, glucocerebrosidase, a chain of a humanized or human antibody, a cytokine, etanercept, tPA, and muteins, fragments, soluble forms, functional derivatives, fusion proteins thereof.

Further examples suitable in accordance with the present invention relate to marker proteins, such as negative or positive selection markers, or amplifiable genes. Examples include proteins selected from adenosine deaminase (ADA), aminoglycoside phosphotransferase (neo), dihydrofolate reductase (DHFR), hygromycin-B-phosphotransferase (HPH), thymidine kinase (tk), xanthine-guanine phosphoribosyltransferase (gpt), multiple drug resistance gene (MDR), ornithine decarboxylase (ODC) and N-(phosphonacetyl)-L-aspartate resistance (CAD), or puromycin actyltransferase (PAC). Further examples include genes used for selection by use of particular metabolic pathways such as galactokinase (Schumperli et al., 1982), the folate receptor (Zhu et al., 2001), or reduced folate carrier (Assaraf et al., 1992). In yet a further preferred embodiment the polypeptide of interest is a reporter gene. Examples are selected from luciferase, green fluorescent protein, alkaline phosphatase, β-galactosidase, or horseradish peroxidase or intramolecular combinations thereof or with other proteins, such as e.g. the Green Fluorescent Protein (GFP) or enhanced GFP (EGFP) with the puromycin acetyl transferase (Abbate et al., 2001).

Preferably, the insulator of the invention is positioned upstream (i.e. in the flanking region 5') and/or downstream (i.e in the flanking region 3') of a DNA sequence coding for a polypeptide of interest, respectively.

In a preferred embodiment, at least two insulators are positioned upstream and downstream of a DNA sequence coding for a polypeptide of interest respectively.

In a further preferred embodiment at least two coding sequences are positioned between the insulators of the invention.

In yet a further preferred embodiment, the two coding sequences code for subunits of a mulitimeric protein.

Co-expression of two subunits of the same protein is particularly advantageous since expression from both promoters may result in production of similar amounts of subunits, or of predetermined ratios of both polypeptides, depending on the strength of the promoters used. The subunits may then assemble in the same cell to form a mature protein.

Preferred examples for dimeric proteins suitable to be expressed using a vector of the invention are the alpha-chain and the beta-chain of a peptide hormone such as human FSH, human LH, human TSH and human CG. The person skilled in the art will appreciate that hormones from other species may be equally used in accordance with the present invention, such as equine, porcine, bovine hormones, for instance, depending on the intended use of the recombinant polypeptide.

In another embodiment of the invention, the first subunit is the heavy chain, and the second subunit is the light chain of an immunoglobulin, or vice versa. A preferred example of a suitable immunoglobulin is an IgG. Such immunoglobulins may e.g. be humanized or human antibodies for therapeutic use. A highly preferred example for such a humanized antibody is a humanized anti-CD11 antibody having the tradename Raptiva®.

In another embodiment of the invention, a gene of interest is co-expressed with a marker or a selection gene (e.g. gene for IL-18BP and gene for PAC or luciferase).

In a third aspect, the invention relates to a host cell comprising the insulator of the invention.

In a fourth aspect of the invention, the host cell is transfected with at least one vector described above. The skilled person will appreciate that the host cell may equally be co-transfected with two or more vectors in accordance with the present invention.

In a fifth aspect of the invention, the host cell and the insulator of the invention are derived from different species. The insulator is derived from chicken DNA, but has been shown to be functional in cells derived from other species such as Chinese Hamster Ovary cells (CHO).

Many host cells are suitable in accordance with the present invention, such as primary or established cell lines from a wide variety of eukaryotes including plant and animal cells, exemplified by CHO, BHK, HEK293 or other immortalized and/or transformed cells.

In a preferred embodiment, the host cell is a CHO cell, and more preferably a CHO-S cell, described e.g. by Shotwell et al. (Shotwell et al., 1982).

In a sixth aspect, the invention relates to a process for the production of a polypeptide of interest comprising the step of transfecting a host cell with at least one vector according to the invention. Depending on the nature of the polypeptide of interest, the process according to the invention leads to a secreted protein that may be harvested from the cell culture supernatant, or to a cell membrane protein or intracellular protein that may be isolated from the cells. Depending on the intended use, the cell itself having the polypeptide integrated may be the product of the process according to the invention.

In a further preferred embodiment, the invention relates to a process for the production of a polypeptide of interest comprising the step of culturing a host cell in accordance with the invention.

In yet a further preferred embodiment, the process further comprises the step of isolating the polypeptide of interest from the host cells. This step is particularly advantageous and easy to carry out for secreted proteins that may be isolated simply from the cell culture supernatant. However, this step equally applies to isolating polypeptides from cellular membranes, or intracellular compartments.

The process of the invention may be used in transient, stable, episomal or viral expression systems. As shown in the Examples below, the vector of the invention resulted in particularly strong expression of the desired protein if used in a stable expression system. Therefore, in a preferred embodiment the transfection is stable transfection.

In a further preferred embodiment, the vector according to the invention is used for expression of a gene of interest.

The use of the vector for the simultaneous expression of two or more genes or cDNAs of interest is also preferred.

In a seventh aspect, the invention relates to the use of a vector of the invention for the manufacture of a medicament for use in plasmid or DNA based therapy or gene therapy.

Having now fully described this invention, it will be appreciated by those skilled in the art that the same can be performed within a wide range of equivalent parameters, concentrations and conditions without departing from the spirit and scope of the invention and without undue experimentation.

While this invention has been described in connection with specific embodiments thereof, it will be understood that it is capable of further modifications. This application is intended to cover any variations, uses or adaptations of the invention following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

EXAMPLES

Figure 1:
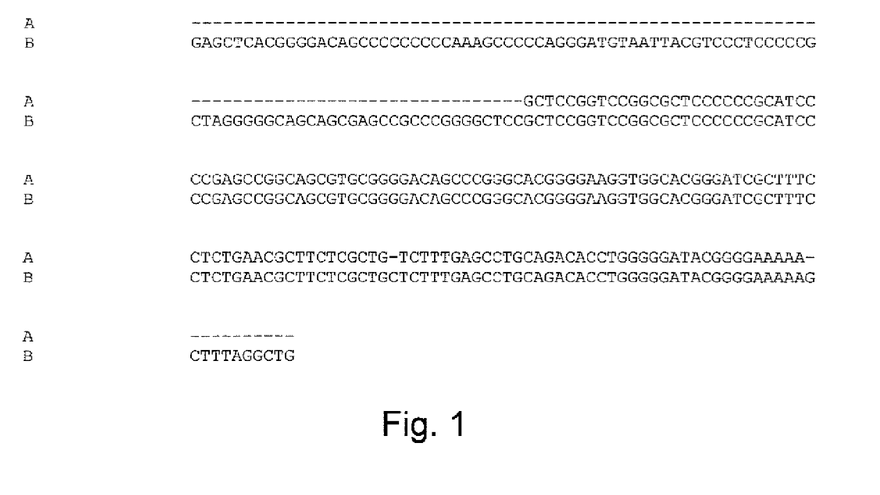
FIG. 1 shows an alignment of the insulator of the invention (A, SEQ ID NO:1) with the prior art 250 bp core insulator region (B, SEQ ID NO:2) of the chicken beta-globin 5'HS4 insulator region.

Example 1
Construction of the Insulator and the Vectors of the Invention
Insulator
The insulator of the invention is 146 bp and has SEQ ID No:1. It comprises 146 bp of the 250 bp core sequence (SEQ ID No: 2) from the 1.2 kb insulator region of the chicken b-globin 5'HS4 locus, as shown in FIG. 1 and is further missing one base pair (around position 107 in alignment). It was assembled by oligonucleotide cloning. The resulting fragment has artificial ends for convenient subcloning.

Vectors
The 146 bp fragment was first duplicated and then cloned in two tandem arrays separated by a multiple cloning site, into the commercial cloning vector pBluescript II SK+ from Stratagene (cat no. 212205-01).

Figure 2:
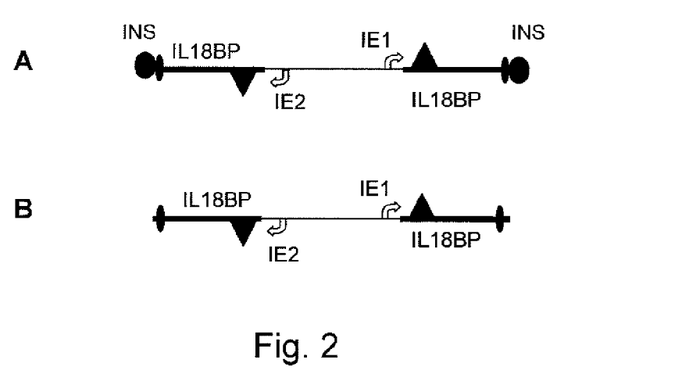
FIG. 2 shows two bi-directional reporter constructs for IL18BP expression. A: IL18BP gene is shown as a bold line and mCMV-IE1 and mCMV-IE2 promoters are indicated as arrows. The triangle represents intron A from the hCMV IE region and the oval represents the polyadenylation signal. Insulator of the invention (filled circle), designated INS, tandem repeat flank each end of the expression cassette. B: same construct devoid of the insulators of the invention sequences.

IL-18BP
A first expression cassette for a marker gene (IL18BP), expressed in two copies from a bi-directional promoter (mCMV-IE1 and mCMV-IE2), was inserted between the two insulator tandems as shown in FIG. 2A. In parallel an otherwise identical control vector devoid of the insulators was constructed as shown in FIG. 2B.

Figure 3:
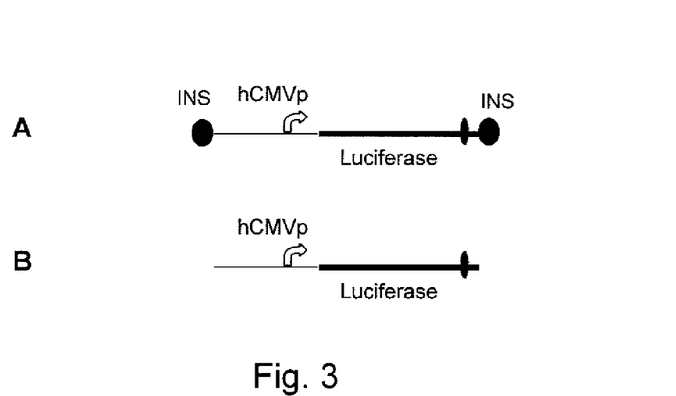
FIG. 3 shows the expression unit for Luciferase. A: Luciferase gene is shown as a bold line and the human CMV promoter (hCMVp) is indicated as an arrow.

Luciferase
In a second approach, a transgene cassette with the firefly luciferase gene expressed from a human CMV promoter was inserted between the insulator tandems (FIG. 3A). Again a control vector without the insulator elements was constructed by inserting the expression cassette in the original backbone vector (pBluescript II SK+, Stratagene, cat no. 212205-01) as shown in FIG. 3B.

Example 2
Insulator Activity in Stably Transfected CHO Cell Pools (IL-18BP)

CHO-S cells were transfected with bi-directional reporter constructs for IL18BP expression according to FIGS. 2A and B.

Materials and Methods
Cells: CHO-S cells from Invitrogen (Cat no: 11619).
Transfection agent: DMRIE-C, Invitrogen, Cat. No. 10459-014.
Vectors:
Insulated and non-insulated IL18BP expression vector described in Example 1.
vector conferring puromycin resistance (puro)
plasmid encoding the selection marker DHFR.
The amounts of vectors used are shown in the following table:

TABLE 1

|  | Insulated | Non-insulated |
| --- | --- | --- |
| IL-18BP expression vector | 33.6 µg | 30 µg |
| Selection plasmid - Puromycin resistance | 3 µg | 3 µg |
| Selection plasmid - DHFR | 3 µg | 3 µg |

Transfection Protocol
CHO-S cells (Invitrogen, Cat no: 11619) were stably transfected using DMRIE-C (Invitrogen, Cat No. 10459-014). Briefly, 40 Mio cells were exposed for four hours to a transfection mix containing the respective expression vector for IL18BP and a vector conferring puromycin resistance as well as a plasmid encoding DHFR. The transfection mix contained the IL18BP expression vector insulated, and the vector conferring resistance to puromycin, as well as the one encoding DHFR in a molar ratio of 10:1:1 respectively. The corresponding amount is 33.6 µg, 3 µg and 3 µg (see Table 1).

In the case of non-insulated IL18BP expression vector, similar molar ratios were used, which correspond to an amount of 30 µg, 3 µg and 3 µg (see Table 1).

All vectors used were previously linearised with a restriction enzyme, PvuI for both IL18BP expression vectors and SspI for both puro and DHFR selection plasmids. After pelleting, the supernatant was removed, and the cells were diluted into serum-free cultivation medium ProCHO-5 (Cambrex) and incubated at 37° C. for 48 hours. Puromycin was then added at a concentration of 10 μg/ml to select for stably transfected cells. Control aliquots were seeded in media containing 10% fetal bovine serum to assess the total number of stable transfectants in the pool by counting colonies growing attached to the plastic surface. Pools for both constructs represent approximately 200,000 independent stable transfectants.

Selective pressure was maintained over 41 days in order eliminate all transfectants with unstable integration sites. Then selective pressure was removed and samples for IL18BP measurements were taken after keeping the cells 14 days without puromycin.

IL-18BP Expression Measurement

IL18BP expression was measured by exposing approximately 1 mio cells to fresh media for 24 hours. Media was then filtered to remove the cells and IL18BP was quantified by a standard ELISA assay in triplicates. The resulting IL18BP titers were used to calculate specific productivities per cell (picogram per cell and day, pcd).

Results

The pool transfected with the insulated expression cassette had a productivity that was elevated more than threefold (3.7 pcd) as compared to the control pool (1.1 pcd).

Example 3

Insulator Activity in Stably Transfected CHO Clones (Luciferase)

Materials and Methods

CHO-S cells (Invitrogen, Cat no: 11619) were stably transfected with the previously mentioned luciferase reporter constructs (see Example 1) using DMRIE-C as transfection agent. A plasmid expressing the puromycin resistance gene was cotransfected using the same protocol as described in Example 2. Two pools were established using 10 μg/ml puromycin. Stable pools were kept under selective pressure for 40 days in order to eliminate cells with unstable integration sites (phase I). The pools were measured for luciferase activity (data not shown) before seeding into 384 well plates using limiting dilution. For each pool seeding was performed both in absence and presence of puromycin in the media. Individual clones were then randomly picked and re-arrayed in 96 well plates to obtain 2 plates for each construct. These clones were then cultivated with or without puromycin for another two months up to a total of three month after limiting dilution with the aim of analysing 96 clones for each construct and condition (phase II).

Luciferase Measurement

The luciferase expression was measured as RLU in stable pools transfected with insulated (I.hCMV Luc.I) or non-insulated (hCMV Luc) constructs in the presence or absence of puromycin (puro). The Bright-Glo™ Luciferase assay system from Promega, Cat No E2610, was used according to the manufacturer's guidelines. Briefly, 50 μl cell suspension was lysed with 50 μl Bright-Glo reagent and incubated for 5 min at room temperature. Luciferase activity was then measured on a Luminometer during 5 seconds/well.

Results

Figure 4:
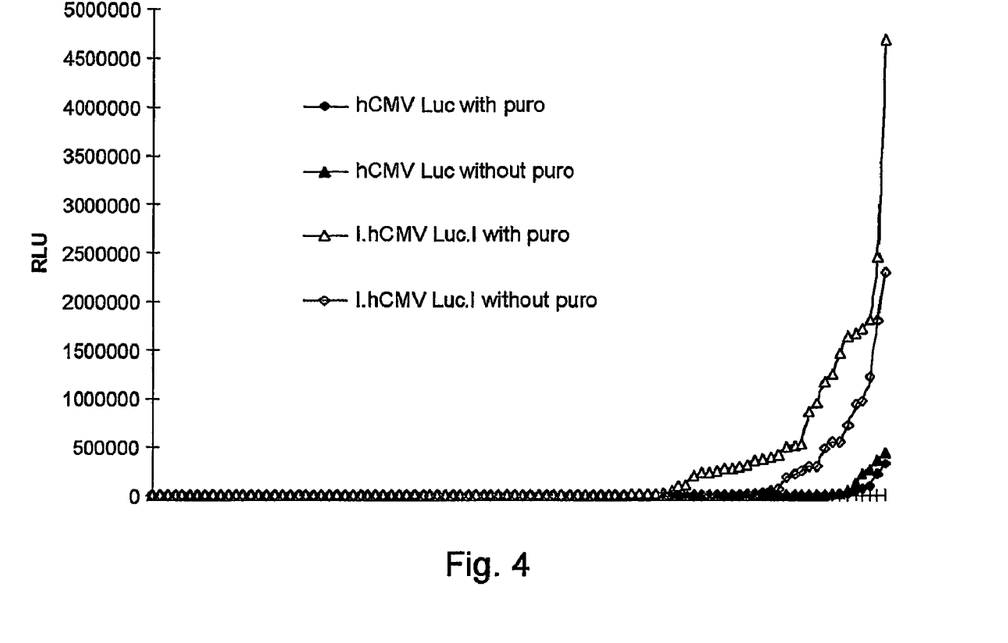
FIG. 4 shows the luciferase expression measured as RLU (relative light units) in stable pools of transfected CHO-S cells in SFM at 3 months after transfection with the insulator of the invention-insulated (I.hCMV Luc.I, FIG. 3A) or non-insulated (hCMV Luc, FIG. 3B) constructs in the presence or absence of puromycin (puro). 96 randomly picked individual clones for each of the four conditions were ranked and plotted by increasing levels of luciferase expression (each increment on the X axis represent one clone).

For each of the conditions tested, I.hCMV Luc.I with puro, I.hCMV Luc.I without puro, hCMV Luc with puro, hCMV Luc without puro, 96 individual clones were ranked and plotted by increasing levels of luciferase expression (see FIG. 4).

The evaluation of expressing clones is summarized in Table 2 for the 4 conditions tested. The numbers of expressing clones (Number of expressors) were counted and the average expression over the selected expressing clones as well as the highest expressing clone are also indicated.

TABLE 2

| Condition | Number of clones tested | Number of expressors | Average expression in RLU | Highest Expression in RLU |
|---|---|---|---|---|
| hCMV Luc with puro | 96 | 9 | 86k | 327k |
| I.hCMV Luc.I with puro | 96 | 41 | 647k | 4690k |
| hCMV Luc without puro | 96 | 11 | 135k | 438k |
| I.hCMV Luc.I without puro | 96 | 25 | 456k | 2290k |

The average luciferase expression measured as RLU level in clones with the insulator of the invention (I.hCMV Luc.I) is on average 5 times higher than in the clones without the insulator. The highest expressing clone I.hCMV Luc.I with puromycin expresses 14 times more Luciferase than the best clone from hCMV Luc with puromycin.

Using the insulator of the invention in the construct increases the number of expressing clones, the average expression level, and the expression level of the highest expressor of the respective series. In absence of selection during phase II, the insulator of the invention increases the probability of identifying expressing clones with long-term stable and elevated expression.

Example 4

Evaluation of a Putative Enhancer Function

An enhancer should be able to enhance expression of a heterologous promoter independently of the orientation and position relative to the promoter. This definition was followed to evaluate a putative enhancer function of the insulator of the invention.

Vector Construction pSV-Luc

This vector which contains only the SV40 promoter and luciferase was derived from pGL3-Ctrl (Promega, E 1741), containing the SV40 promotor driving the Luciferase gene, and SV40 enhancer located in 3' of the gene, and pGL3-Basic (Promega, E1751), lacking both promoter and enhancer. Briefly pGL3-ctrl was cut by NotI/XbaI, to isolate a fragment containing the SV40 promoter, followed by the Luciferase gene.

In a similar way, pGL3-basic was cut by NotI/XbaI and the vector backbone containing the poly A region, without the 3' enhancer, was isolated. pSV-Luc was obtained by combining both fragments.

pBS(2Ins)2.2

Briefly, oligonucleotides were designed based on the insulator of the invention and the resulting fragment was digested by XbaI/SpeI and cloned into pBluescript II SK+, Stratagene (cat no. 212205-01), also digested by XbaI/SpeI (step 1). A tandem repeat of the insulator of the invention fragment was cloned by opening the vector obtained in step 1, by XbaI, and inserting a second insulator of the invention fragment digested by XbaI/SpeI (step 2). Sequence and orientation were checked before duplication of the insulator tandem repeat. The second tandem repeat was cloned in the Acc65I site, blunt-ended by Klenow enzyme of the vector obtained in step 2. The Insulator of the invention was then obtained by digesting the vector of step 2 by XbaI/SpeI, blunt-ended by Klenow enzyme. The vector obtained is called pBS(2Ins)2.2.

pIns(2) SV-Luc and its Reverse Oriented Version, pIns(2) revSV-Luc

One unit of insulator sequence, which comprises one tandem repeat (2× insulator of the invention) was isolated, by digesting pBS(2Ins)2.2 by SpeI/XbaI. The recipient vector is pSV-Luc opened by NheI. As the sites used for digestion are compatible, the cloning reaction gives vectors with both orientations.

Transient Transfection

Materials and Methods

CHO-S, Invitrogen (Cat no: 11619).

Plasmid DNAs listed below (see above section for vectors construction) were isolated from overnight growing standard culture with Nucleobond PC 500 kit (Macherey-Nagel Cat. No: 740 574) according to the protocol provided by the manufacturer:

DNAs to be evaluated: plns(2)-SV-Luc and its reverse oriented version, plns(2)revSV-Luc DNAs control pSV-Luc: expression from the SV40 promoter in absence of any enhancer sequence.

pGL3-ctrl: expression from the SV40 promoter as well as the SV40 enhancer located 3' of the gene.

Transfection

Lipofectamine (Invitrogen, Cat No: 18324-012)

Format: 24 well plates.

Cells: CHO-S in exponential growth phase, to ensure that the cells are in good shape, are passaged 24 h before transfection. To avoid a stationary phase at low cell density, cells are diluted to $0.75 \times 10^6$ cells/ml. The total amount of cells to be transfected is $1.5 \times 10^5$, resuspended in 100 µl ProCho5, (Cambrex, Cat No: B-12766Q) per well, in 24 well plate.

Transfection Mixes were as follows: (for 1 well note that a mastermix is made taking 3.3× the volumes indicated below, such as triplicate assays can be performed)

A) Lipofectamine: 2 µl
ProCho5 Medium: 48 µl
Total volume is 50 µl.

B) DNAs: 1 µg,
ProCho5 Medium: complement to 50 µl.

Solutions A and B were mixed and incubated for 30 min at room temperature.

This mix was added to the 100 µl ProCho5 Medium containing $1.5 \times 10^5$ cells. The cells were placed back in an incubator and incubated at 37° C., 5% $CO_2$ for 3 hours. Then, 400 µl ProCho5 Medium were added in order to dilute Lipofectamine. The cells were incubated for another 48 hours before sampling for analysis. All transfections were carried out in triplicate.

Mock transfection: It corresponds to untransfected cells and gives background level indication.

Luciferase Measurement

The Bright-Glo Luciferase assay system from Promega (Cat No: E2610) was used according to the manufacturer's guidelines.

Briefly, the cell suspension was homogenized by pipetting up and down several times, and an aliquot of 50 µl was taken out and put in a white 96 well plate (Nunc, Cat no: 236108). 50 µl of reconstituted Bright-Glo Reagent were directly added and the mixture was incubated 5 min at room temperature. Light emission was measured on a Centro LB 960 luminometer (Berthold Technologies) during 5 seconds of acquisition time. Normalization by an internal control or total protein level was not made, but variation within the triplicates provides sufficient indication for comparable transfection efficiency.

Results

Figure 5:
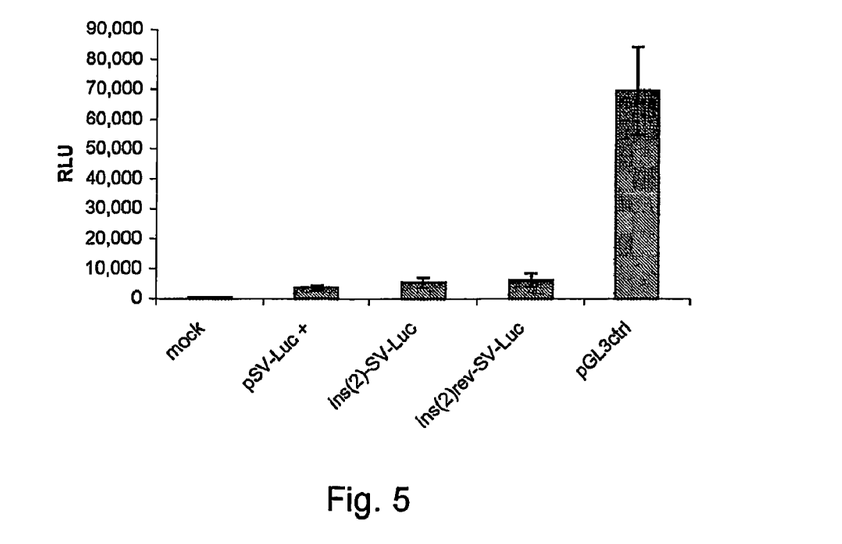
FIG. 5 Shows luciferase expression measured as RLU (relative light units) in CHO-S cells transiently transfected with plns(2)-SV-Luc, plns(2)revSV-Luc, pSV-Luc, pGL3-ctrl constructs, or mock transfected.

The results of the luciferase expression driven by the different plasmid DNA are reported in FIG. 5.

The data clearly indicate that there is no enhancer function within the insulator of the invention sequence. No significant increase in expression level is observed when the insulator is added to the pSV-Luc, in sense or reverse orientation.

Conclusions

From the above examples, the following conclusions can be drawn:

The insulator of the invention displays strong insulator activity in CHO cells;

The number of expressing clones is higher (5 fold increased chance/probability of identifying expressing clones);

Expression level of expressing clones in high;

The presence of the insulator of the invention increases the chances of obtaining stable long-term expression.

The insulator of the invention does not contain enhancer activity.

Reference List

Abbate, J., Lacayo, J. C., Prichard, M., Pari, G., and McVoy, M. A. (2001). Bifunctional protein conferring enhanced green fluorescence and puromycin resistance. Biotechniques 31, 336-340.

Assaraf, Y. G., Feder, J. N., Sharma, R. C., Wright, J. E., Rosowsky, A., Shane, B., and Schimke, R. T. (1992). Characterization of the coexisting multiple mechanisms of methotrexate resistance in mouse 3T6 R50 fibroblasts. J Biol Chem 267, 5776-5784.

Bell, A. C., West, A. G., and Felsenfeld, G. (1999). The protein CTCF is required for the enhancer blocking activity of vertebrate insulators. Cell 98, 387-396.

Blackwood, E. M. and Kadonaga, J. T. (1998). Going the distance: a current view of enhancer action. Science 281, 61-63.

Chung, J. H., Bell, A. C., and Felsenfeld, G. (1997). Characterization of the chicken beta-globin insulator. Proc Natl Acad Sci USA 94, 575-580.

Chung, J. H., Whiteley, M., and Felsenfeld, G. (1993). A 5' element of the chicken beta-globin domain serves as an insulator in human erythroid cells and protects against position effect in *Drosophila*. Cell 74, 505-514.

Ciana, P., Di Luccio, G., Belcredito, S., Pollio, G., Vegeto, E., Tatangelo, L., Tiveron, C., and Maggi, A. (2001). Engineering of a mouse for the in vivo profiling of estrogen receptor activity. Mol Endocrinol. 15, 1104-1113.

de Wet, J. R., Wood, K. V., Helinski, D. R., and DeLuca, M. (1985). Cloning of firefly luciferase cDNA and the expression of active luciferase in *Escherichia coli*. Proc Natl Acad Sci USA 82, 7870-7873.

Izumi, M. and Gilbert, D. M. (1999). Homogeneous tetracycline-regulatable gene expression in mammalian fibroblasts. J Cell Biochem 76, 280-289.

Li, Q., Harju, S., and Peterson, K. R. (1999). Locus control regions: coming of age at a decade plus. Trends Genet 15, 403-408.

Mazumder, B., Seshadri, V., and Fox, P. L. (2003). Translational control by the 3'-UTR: the ends specify the means. Trends Biochem Sci 28, 91-98.

Mountford, P. S. and Smith, A. G. (2003). Translational control by the 3'-UTR: the ends specify the means Internal ribosome entry sites and dicistronic RNAs In mammalian transgenesis. Trends Genet. 28, 91-98.

Recillas-Targa, F., Pikaart, M. J., Burgess-Beusse, B., Bell, A. C., Litt, M. D., West, A. G., Gaszner, M., and Felsenfeld, G. (2002). Position-effect protection and enhancer blocking by the chicken beta-globin insulator are separable activities. Proc Natl Acad Sci USA 99, 6883-6888.

Schumperli, D., Howard, B. H., and Rosenberg, M. (1982). Efficient expression of *Escherichia coli* galactokinase gene in mammalian cells. Proc Natl Acad Sci USA 79, 257-261.

Shotwell, M. A., Mattes, P. M., Jayme, D. W., and Oxender, D. L. (1982). Regulation of amino acid transport system L in Chinese hamster ovary cells. J Biol Chem 257,2974-2980.

Wood, K. V., de Wet, J. R., Dewji, N., and DeLuca, M. (1984). Synthesis of active firefly luciferase by in vitro translation of RNA obtained from adult lanterns. Biochem Biophys. Res. Commun. 124, 592-596.

Zhu, W. Y., Allegro, M. A., and Melera, P. W. (2001). The rate of folate receptor alpha (FR alpha) synthesis in folate depleted CHL cells is regulated by a translational mechanism sensitive to media folate levels, while stable overexpression of its mRNA Is mediated by gene amplification and an increase in transcript half-life. J Cell Biochem 81, 205-219.

The invention claimed is:

1. A method of expressing a gene of interest in a Chinese Hamster Ovary (CHO) cell comprising
culturing a CHO cell comprising a vector under conditions that allow for the expression of said gene of interest,
said vector comprising a promoter, a DNA encoding at least one gene of interest and one or more chromatin insulators consisting of SEQ ID NO: 1 and wherein said CHO cell expresses the gene of interest.

2. The method according to claim 1, wherein the vector further comprises
an enhancer or a functional expressing enhancing fragment thereof.

3. The method according to claim 1, wherein said vector further comprises one or more DNA sequences coding for regulatory elements selected from 5'UTRs, introns, 3'UTRs, mRNA 3' end processing sequences, polyadenylation sites, and internal ribosome entry sequences (IRES).

4. The method according to claim 1, wherein the DNA encodes more than one polypeptide of interest through a polycistronic mRNA.

5. The method according to claim 1, wherein said vector further comprises one or more DNA elements selected from boundary elements, locus control regions (LCRs), matrix attachment regions (MARs), and elements for recombination and cassette exchange.

6. The method according to claim 1, wherein the promoter is selected from the group consisting of a viral promoter, a phage promoter, mCMV-IE1, mCMV-IE2, hCMV, SV40, RSV, T7, T3, and a functional expression promoting fragment thereof.

7. The method according to claim 1, wherein the gene of interest encodes a polypeptide of interest selected from the group consisting of FSH, LH, CG, TSH, a growth hormone, an interferon, TNF binding protein I, TNF binding protein II, IL-18BP, IL-6, IFNAR1, LIF, a mutein, a fragment thereof, a functional derivative thereof, and a fusion protein thereof.

8. The method according to claim 1, wherein the gene of interest encodes a polypeptide of interest selected from the group consisting of EPO, G-CSF, GM-CSF, a chain of a humanized antibody, a cytokine, a coagulation factor, etanercept, tPA, an integrin, a mutein, a fragment thereof, a functional derivative thereof, and a fusion protein thereof.

9. The method according to claim 1, wherein the gene of interest encodes a polypeptide of interest selected from the group consisting of adenosine deaminase (ADA), aminoglycoside phosphotransferase (neo), dihydrofolate reductase (DHFR), hygromycin-B-phosphotransferase (HPH), thymidine kinase (tk), xanthine-guanine phosphoribosyltransferase (HPH), multiple drug resistance gene (MDR), ornithine decarboxylase (ODC) N-(phosphonacetyl)-L-aspartate resistance (CAD), puromycin acetyltransferase (PAC), galactokinase, human folate receptor, and a reduced folate carrier.

10. The method according to claim 1, wherein the gene of interest encodes a polypeptide of interest selected from the group consisting of luciferase, green fluorescent protein, alkaline phosphatase, horseradish peroxidase, and a combination thereof.

11. The method according to claim 1, wherein one insulator is positioned upstream and one insulator is positioned downstream of the gene of interest.

12. The method according to claim 1, wherein at least two insulators are positioned upstream and downstream of the gene of interest, respectively.

13. The method according to claim 1, wherein at least two protein encoding sequences are positioned between the insulators.

14. The method according to claim 13, wherein the at least two coding sequences code for subunits of a multimeric protein.

15. The method according to claim 14, wherein the multimeric protein is a hormone comprising a first subunit that is the alpha chain and a second subunit that is the beta chain of a hormone selected from the group consisting of: human FSH, human LH, human TSH, and human CG.

16. The method according to claim 14, wherein the multimeric protein is an antibody comprising a first subunit that is the heavy chain of an immunoglobulin and a second subunit that is the light chain of an immunoglobulin.

17. The method according to claim 1, wherein said CHO cell simultaneously expresses two or more genes of interest from the vector.

18. The method according to claim 1, further comprising the step of isolating the polypeptide of interest from the CHO cells.

19. The method according to claim 7, wherein said protein of interest is IL-18BP.

* * * * *

UNITED STATES PATENT AND TRADEMARK OFFICE
CERTIFICATE OF CORRECTION

PATENT NO. : 8,133,699 B2
APPLICATION NO. : 10/576509
DATED : March 13, 2012
INVENTOR(S) : Philippe Chatellard and Markus Imhof It is certified that error appears in the above-identified patent and that said Letters Patent is hereby corrected as shown below:

Column 13,
Line 8, "Allegro, M.A.," should read --Alliegro, M.A.,--.
Line 12, "mRNA Is mediated" should read --mRNA is mediated--.
Line 58, "functional expressing enhancing fragment" should read
    --functional expression enhancing fragment--.

Column 14,
Line 48, "LIF, a mutein, a fragment thereof" should read
    --LIF, a mutein thereof, a fragment thereof--.
Line 54, "an integrin, a mutein, a fragment thereof" should read
    --an integrin, a mutein thereof, a fragment thereof--.

Signed and Sealed this
Thirty-first Day of July, 2012

David J. Kappos
*Director of the United States Patent and Trademark Office*